United States Patent [19]
Friauf et al.

[11] Patent Number: 5,295,746
[45] Date of Patent: Mar. 22, 1994

[54] HIGH RESOLUTION DIGITAL THERMOMETER

[75] Inventors: Walter S. Friauf, Bethesda; Thomas R. Clem, Sr., Silver Spring; Robert L. Berger, Bethesda, all of Md.

[73] Assignee: The United States of America as represented by the Secretary of the Department of Health and Human Services, Washington, D.C.

[21] Appl. No.: 831,603

[22] Filed: Feb. 5, 1992

[51] Int. Cl.⁵ .................... G01N 25/00; G06F 7/02
[52] U.S. Cl. ................. 374/170; 364/571.03; 364/571.04; 374/10; 374/114; 374/171
[58] Field of Search ............ 374/170, 171, 114, 10; 364/571.03, 571.04

[56] References Cited

U.S. PATENT DOCUMENTS

| | | | |
|---|---|---|---|
| 3,620,082 | 11/1971 | Peters | 374/170 |
| 3,722,283 | 3/1973 | Treharne et al. | 374/170 |
| 3,781,869 | 12/1973 | Sudnick et al. | |
| 3,791,214 | 2/1974 | Keith | |
| 3,872,728 | 3/1975 | Joyce et al. | |
| 3,950,991 | 4/1976 | Grass | 374/114 |
| 4,022,063 | 5/1977 | West et al. | |
| 4,126,042 | 11/1978 | Lynch | |
| 4,143,549 | 3/1979 | Koehler | 374/114 |
| 4,443,117 | 4/1984 | Muramoto et al. | |
| 4,607,962 | 8/1986 | Nagao et al. | 374/170 X |
| 4,618,848 | 10/1986 | Parfitt | |
| 4,642,785 | 2/1987 | Packard et al. | |
| 4,679,162 | 7/1987 | Ferber et al. | |
| 4,814,692 | 3/1989 | Baumann | |
| 5,064,296 | 11/1991 | Huijsing et al. | 374/170 X |

*Primary Examiner*—Daniel M. Yasich
*Attorney, Agent, or Firm*—Lowe, Price, LeBlanc & Becker

[57] ABSTRACT

A high resolution digital thermometer capable of measuring temperature differences on the order of several micro-degrees centigrade. The device includes a bridge circuit having two thermistors in series. An output of the bridge circuit feeds a signal to an analog-to-digital convertor via a high gain amplifier. A computer maintains the balance of the bridge circuit to avoid a situation wherein the range of the analog-to-digital convertor would be exceeded.

13 Claims, 2 Drawing Sheets

HIGH RESOLUTION DIGITAL THERMOMETER

TECHNICAL FIELD

The present invention relates to temperature measuring and recording devices and methods. More particularly, the present invention relates to temperature measuring and recording devices and methods which measure temperature differences to an accuracy of several micro-degrees centigrade.

BACKGROUND ART

A number of digital thermometers exist which have accuracy limitations on the order of one to one hundred milli-degrees centigrade. The accuracy limitations of such digital thermometers is mainly due to quantizing error and noise of analog-to-digital convertors which follow thermistor bridges, or by inherent limitations associated with other arrangements and techniques.

The follow U.S. patents are considered by applicants to represent the closest state of the art.

U.S. Pat. No. 3,781,869 to Sudnick et al discloses a transducer amplifier with automatic balance for strain gages and other transducers in quarter, half or full bridge configurations which provides an analog output suited for measurement, control or display purposes. The amplifier includes temperature compensation provided by a silicon PN junction whose voltage-temperature characteristic is used to effect the offset of an integrated circuit amplifier stage. A signal for zero balance is derived from the amplifier output which is sampled and retained in an analog to digital converter and reconverted to analog form.

U.S. Pat. No. 3,791,214 to Keith discloses a digital clinical thermometer which includes a thermistor scaling amplifier 9 having a thermistor which is a temperature sensitive transducer.

U.S. Pat. No. 3,872,728 to Joyce et al discloses a clinical thermometer. The instrument is calibrated by placing a known resistance in a bridge circuit in place of the resistance of the line cord and the resistance within tip 36 of probe 30.

U.S. Pat. No. 4,022,063 to West et al discloses an electromechanical digital thermometer. In operation, temperature probe 10 is placed in a patient's mouth causing the thermistor therein to change resistance. This causes unbalance in bridge 13 amplified by amplifiers 14 and 15 and thus driving motor 21. Shaft 25 then takes up a new position until resistance of potentiometer 26 fed back to the bridge balances the new value of the thermistor resistance. The angular portion of the shaft 25 and coding disc 22 is indicative of the temperature of the thermistor.

U.S. Pat. No. 4,126,042 to Lynch discloses an error compensating network for a digital display thermometer in which a thermocouple is connected to one input of a differential amplifier disposed in a feedback configuration with a voltage-to-current converter for providing a signal current that is a measure of the temperature within a region being monitored by the thermocouple junction. A terminal of the thermocouple outside of the monitored region is directly connected through voltage dividing resistors to the differential amplifier and an active element of the converter to nullify the error introduced by ambient temperature variations.

U.S. Pat. No. 4,443,117 to Muramoto et al discloses a measuring apparatus wherein an amplifier is connected between a bridge circuit and an analog to digital converter followed by a data processor and display device.

U.S. Pat. No. 4,618,848 to Parfitt discloses an analog to digital converter circuit which uses a CMOS multiplexer, an analog to digital convertor and an operational amplifier buffer which is controlled by a single chip microprocessor.

U.S. Pat. No. 4,642,785 to Packard et al discloses a cordless electronic thermometer with a bridge circuit consisting of a thermistor 38 and resistors 35, 36 and 37, which feeds a signal to an analog to digital converter. A memory unit is provided for storing temperature data. A processing unit is provided for calculating the temperature of a patient.

U.S. Pat. No. 4,679,162 to Ferber et al discloses a wide range linear to log converter with a microcomputer control. The microcomputer provides slope corrections and applies the output corrections for offsets due to the circuit components and ambient temperature compensation for increased precision.

U.S. Pat. No. 4,814,692 to Baumann discloses a circuit for measuring and digitizing the value of a resistance. The resistance to be measured is both a component of an A/D converter which operates in accord with the charge balancing network and is also a component of the resistance network bridge. The circuit permits both a pure resistance measurement and attainment of a composite measured value from a plurality of measured values.

In spite of the developments and advance in the prior art, there remains a need for a high resolution digital thermometer capable of measuring temperature difference on the order of several micro-degrees centigrade.

DISCLOSURE OF THE INVENTION

It is accordingly one object of the present invention to provide a device for measuring temperature differences.

Another object of the present invention is to provide a device for measuring temperature differences to an accuracy of several micro-degrees centigrade.

A further object of the present invention is to provide a device for measuring temperatures which can be used in chemical and biological analysis.

An even further object of the present invention is to provide a method of measuring temperature differences.

A still further object of the present invention is to provide a method of measuring temperatures to an accuracy of several micro-degrees centigrade.

According to these and further objects of the present invention which will become apparent as the description thereof proceeds, the present invention provides a high resolution digital thermometer which includes:

a bridge circuit;

first and second thermistors arranged in series in the bridge circuit;

a high gain amplifier connected to an output of the bridge circuit;

an analog-to-digital converter connected to an output of the high gain amplifier; and a computer means for initiating and maintaining the bridge circuit in a balanced state.

The present invention further provided an improvement for prior art devices which measure temperature differences between two thermistors in a bridge circuit which improvement involves the incorporation of a computer means for initiating and maintaining the bridge circuit in a balanced state.

In addition, the present invention provides a method of measuring temperature differences which comprises:

providing a bridge circuit containing first and second thermistors, wherein an output of the bridge circuit is connected to a high gain amplifier and an output of the high gain amplifier is connected to an analog-to-digital converter;

balancing the bridge circuit with a computer means;

exposing the second thermistor to a thermal environment different from that of the first thermistor; and determining temperature differences between the first and second thermistors from the output of the analog-to-digital converter.

BRIEF DESCRIPTION OF DRAWINGS

The present invention will be described with reference to the attached drawings which are given by way of non-limiting examples only in which.

BEST MODE FOR CARRYING OUT THE INVENTION

The present invention is directed to devices and methods for measuring and recording temperature differences with an accuracy of several micro-degrees centigrade, as a function of time. The temperature differences are measured between two thermistors in a bridge circuit as discussed in detail below.

Because the present invention utilizes two thermistors between which temperature differences are measured, the present invention is particularly advantageous when the two thermistors are in reference and test positions in apparatus for chemical and/or biochemical analysis. For example, in the case of chemical analyzers, one of the thermistors may be positioned in thermal contact with a reaction mixture of interest while the other thermistor may be maintained in thermal contact with a standard or reference solution. Measured temperature differences between the reaction mixture and the standard or reference solution can therefore be used to detect or monitor heats of reactions.

The present invention involves a device in which a high gain amplifier is provided between a bridge circuit and an analog-to-digital converter as discussed below in reference to the drawings. According to the present invention, this arrangement has been found to effectively reduce quantizing error by a factor equal to the gain of the amplifier. However, since this arrangement also increases the likelihood that the range of the analog-to-digital converter will be exceeded, the present invention incorporates a computer which is utilized to insure that the bridge circuit is balanced and remains very close to being balance at all times.

Although the primary function of the computer is to initiate and maintain the balance of the bridge circuit, the computer can also be utilized for a number of other purposes which enhance the accuracy and ease of use of the device. For example, the computer can be utilized to automatically set the power dissipation of the thermistors to a desired rate, to automatically correct for linearly time varying thermo-electric potentials, to automatically initially balance the bridge circuit, to automatically acquire data at desired sampling rates, to determine absolute as well as differential temperature, and provide for easy recall, display, and print out of tabular and graphical test results.

Figure 1:
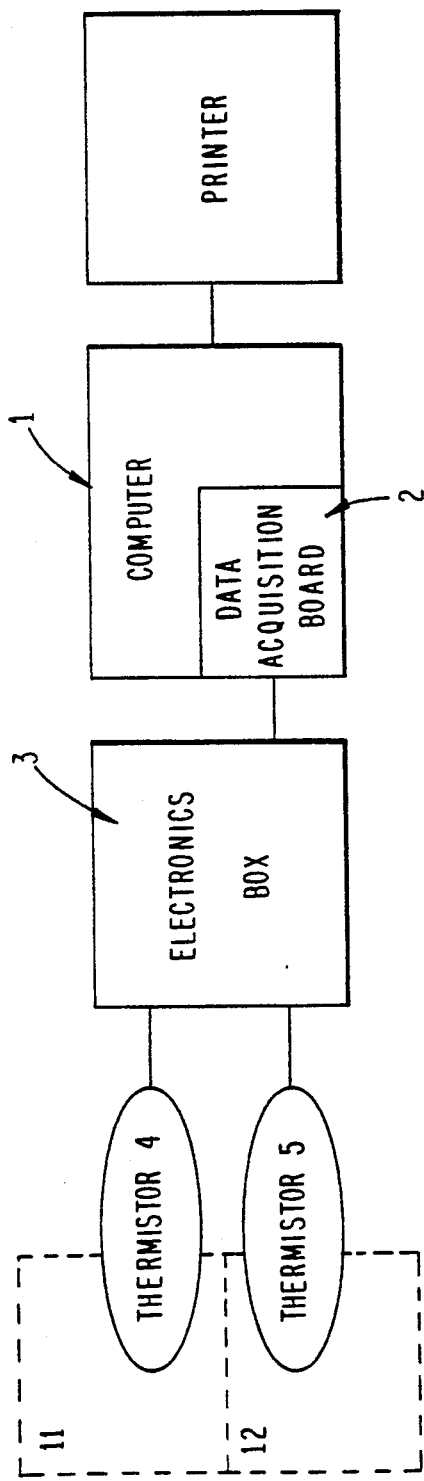
FIG. 1 is a block diagram which shows the major components of a temperature measuring device according to one embodiment of the present invention.

The device according to one embodiment of the present invention is shown in FIG. 1. As shown, the device includes a computer means 1, e.g., a personal computer (PC), a standard commercially available data acquisition board 2 (e.g., Data Translations Corp, Model No. 2823) which is installed in the computer 1, an electronics box 3 which houses a high gain amplifier and other circuit components discussed in detail below, and two thermistors 4 and 5.

The two thermistors 4 and 5 are illustrated schematically; however, it is to be understood that the two thermistors may, according to one embodiment, be fixed to a common probe assembly which maintains the thermistors at a preset or adjustable distance from one another. In other embodiments, the thermistors may be unconnected from one another (other than through the elements of the electronic section), so that the thermistors may be positioned as desired in test/reference positions, e.g., chambers, reactors, flow lines, or the like.

The operation of the device requires the use of one or more software packages, including standard software packages which are packaged with commercial personal computers and commercial acquisition boards (e.g., Quinn-Curtis Science and Engineering Package). The function of these and other software programs utilized are described below. From the described operation of the device which is presented below, one skilled in the art having basic computer programing skills can easily provide the necessary programing required to operate the device.

Figure 2:
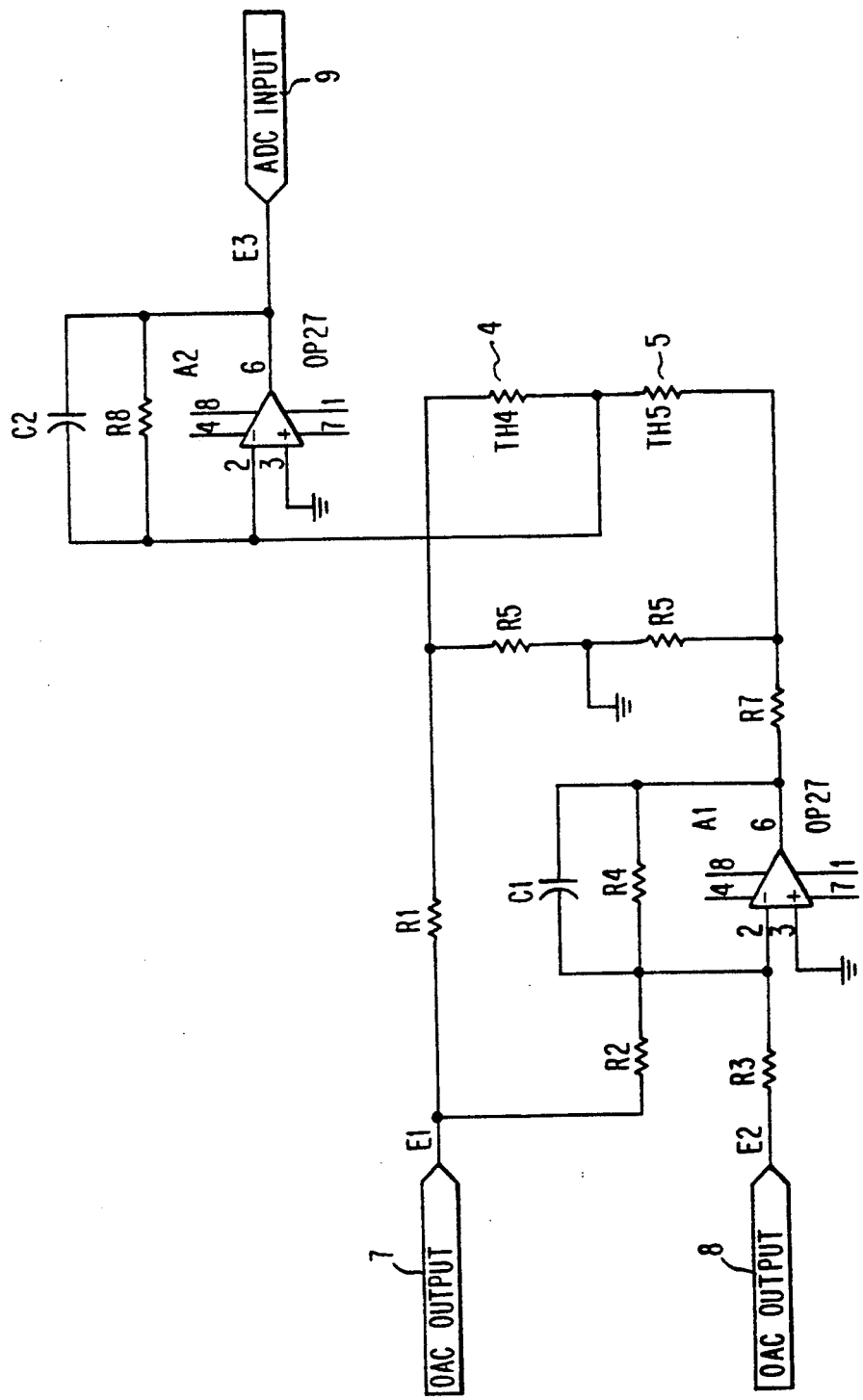
FIG. 2 is a schematic diagram showing the electrical components of a temperature measuring device according to one embodiment of the present invention.

The electronics section is shown schematically in FIG. 2. The electronics section includes two thermistors 4 and 5. These two thermistors 4 and 5 should be matched with respect to their temperature coefficients. Moreover, the resistance of the two thermistors 4 and 5 at the same temperature should be fairy closely matched so that the self-heating effect of each thermistor will be about the same.

The thermistors 4 and 5 are positioned in a bridge circuit as illustrated. The common junction between thermistors 4 and 5 is connected to the inverting input of operational amplifier A2, which maintains this input at virtual ground potential as a result of feedback through resistor R8, and the connection of the non-inverting input to the ground. Thermistor 4 is excited by the output of digital-to-analog converter 7 which is attenuated by R1 and R5 so that the full dynamic range of the digital-to-analog converter 7 can be utilized at the low excitation voltages needed for very low power operation of the thermistors.

Thermistor 5 is also excited by the output of digital-to-analog convertor 7; however, the output of digital-to-analog convertor 7 is inverted in polarity by amplifier A1 and resistors R2 and R4, and attenuated by resistors R7 and R6. Thus, if the output of digital-to-analog converter 8 is zero, the voltage applied to thermistor 5 will be equal and opposite to that applied to thermistor 4, and the bridge circuit will be balanced if the two thermistors are exactly equal. The voltage out of digital-to-analog converter 7 needed to provide a specific power dispensation in thermistor 4 is calculated and applied by the computer means. This voltage calculation is based upon a nominal resistance value entered by the operator.

In general, the two thermistors will not be exactly equal, since they must have very closely matched temperature coefficients, and it is not practical to also match other characteristics and parameters very closely. Consequently, the bridge will not be balanced with equal but opposite voltages applied to the two thermistors. In order to bring the bridge into balance, the output of digital-to-analog converter 8 is made non-zero. This changes the voltage applied to thermistor 5, but does not affect the voltage applied to thermistor 4. The output of digital-to-analog converter 8 is adjusted by the computer means to reduce the output reading of analog-to-digital converter 9 to the lowest possible value utilizing an iterative procedure. It is noted that E3 cannot be exactly zero because the output of the digital-to-analog converter 8 changes in discrete steps. This however is not a problem because any residual voltage is subtracted from all subsequent readings.

The bridge circuit is then ready to measure small differential temperature changes. However, the common temperature is measured first by making a moderate known change in the output of digital-to-analog converter 8 and noting the resulting change in the output of analog-to-digital converter 9. Since the value of R8 is known, the value of thermistor 5 can be calculated (by the computer means), providing the information needed to determined the temperature. The value of thermistor 4 can also be calculated, allowing power dissipation in it to be determined exactly, and this can be readjusted if desired.

Before taking data, both E1 and E2 are set to zero and a baseline reading out of the analog-to-digital convertor 9 is recorded. Ideally this value would be zero, but in practice it will usually not be zero because of offset in amplifier A2 as well as various thermo-electric potentials of the components. After the baseline reading of the analog-to-digital convertor 9 is recorded, E1 and E2 are restored to the values previously determined. Next, thermistor 5 is positioned as desired in a test location 12, e.g., in thermal contact with an environment whose temperature is to be measured, and a desired number of readings of the output of the analog-to-digital converter 9 are acquired at a predetermined rate. When the desired rate while thermistor 4 is maintained in contact with a reference or standard environment 11 is lower than the maximum rate of the analog-to-rate digital convertor 9, multiple measurements can be made and averaged for each data point, thus minimizing noise.

Immediately following the final data reading, E1 and E2 are again set to zero and the output of the analog-to-digital convertor 9 is read. This allows a correction for thermo-electric potentials to be interpolated throughout the run to accommodate a linear variation with time. For a very long run when there might be concern that changes might not be linear, additional zero points can be taken during the run.

The actual differential temperature change is calculated by the computer by taking the log of one plus the corrected reading of the output of analog-to-digital converter 9 (reading minus baseline) and scaling to account for circuit constants and the thermistor temperature coefficient.

In operation as described above, neither E1 nor E2 changes during the run. However, if a temperature change occurred which threatened to exceed the linear range of the analog-to-digital convertor 9, this would be sensed by the computer in a preferred embodiment and E2 would be adjusted one or more times during the run so as to keep the output in the linear range, with the voltage shift being added to each reading.

A prototype of one embodiment of the present invention as shown in FIG. 2 was built with the following component characteristics, listed in Table I below. It is emphasized that the present invention is not to be considered as being limited to the components of the prototype which are listed in Table I since it is clear that components having different characteristics could be utilized in the device according to the present invention as disclosed.

TABLE I

| | |
|---|---|
| TH4 | 5K; −4%/C |
| TH5 | 5K; −4%/C |
| A1 | OP27 |
| A2 | OP27 |
| C1 | 470 pfd |
| C2 | 100 pfd |
| R1 | 2K; 0.1% |
| R2 | 10K; 0.1% |
| R3 | 100K; 0.1% |
| R4 | 10K; 0.1% |
| R5 | 100K; 0.1% |
| R6 | 100K; 0.1% |
| R7 | 2K; 0.1% |
| R8 | 10M; 0.1% |

Although the present invention has been described with reference to particular means, material and embodiments, from the foregoing description, one skilled in the art can easily ascertain the essential characteristics of the present invention and various changes and modifications may be made to adopt the various uses and conditions without departing from the spirit and scope of the present invention as described by the claims which follow.

What is claimed is:

1. A high resolution digital thermometer which comprises:
    a bridge circuit;
    first and second thermistors arranged in series in said bridge circuit;
    a high gain amplifier connected to an output of said bridge circuit;
    an analog-to-digital converter connected to an output of said high gain amplifier; and
    a computer means for initiating and maintaining said bridge circuit in a balanced state.

2. A high resolution digital thermometer according to claim 1, wherein said computer means includes a means for supplying control signals to said bridge circuit, means to receiving output signals from said bridge circuit and means for calculating temperature differences between said first and second thermistors.

3. A high resolution digital thermometer according to claim 2, further including a means to output information from said computer means.

4. A high resolution digital thermometer according to claim 1, wherein said first and second thermistors are positioned respectively in test and reference positions in a chemical analyzer.

5. A high resolution digital thermometer according to claim 1, wherein said first and second thermistors are positioned respectively in test and reference positions in a biological analyzer.

6. In a device for measuring temperature differences between two thermistors in a bridge circuit, the improvement comprising a computer means for initiating and maintaining said bridge circuit in a balanced state, wherein said computer means includes a means for supplying control signals to said bridge circuit, means for receiving output signals from said bridge circuit and means for calculating temperature differences between said thermistors.

7. A device for measuring temperature differences between two thermistors according to claim 6, further including a means for outputting information from said computer means.

8. A method of measuring temperature differences which comprises:
providing a bridge circuit containing first and second thermistors, wherein an output of said bridge circuit is connected to a high gain amplifier and an output of said high gain amplifier is connected to an analog-to-digital converter;
balancing said bridge circuit with a computer means;
exposing said second thermistor to a thermal environment different from that of said first thermistor; and
determining temperature differences between the first and second thermistors from the output of said analog-to-digital converter.

9. A method of measuring temperature differences according to claim 8, wherein said thermal environment to which said second thermistor is exposed comprises a biological reaction.

10. A method of measuring temperature differences according to claim 8, wherein said computer means initiates and maintains said bridge circuit in a balance state.

11. A method of measuring temperature differences according to claim 8 wherein temperature differences on the order of $1 \times 10^{-6°}$ to $1 \times 10^{-5°}$ C. are determined.

12. A method of measuring temperature differences according to claim 8, further including an initial calibration step wherein said second thermistor is substituting with a known resistance, a known voltage is applied to the first thermistor and a voltage is applied to balance the bridge circuit.

13. A method of measuring temperature differences according to claim 8, wherein said thermal environment to which said second thermistor is exposed comprises a chemical reaction.

* * * * *